(12) United States Patent
Kassel et al.

(10) Patent No.: US 12,194,287 B2
(45) Date of Patent: Jan. 14, 2025

(54) METHOD OF MANUFACTURING ELECTRICAL CONDUCTOR TRACKS IN A REGION OF AN INTRAVASCULAR BLOOD PUMP

(71) Applicant: KARDION GMBH, Stuttgart (DE)

(72) Inventors: Julian Kassel, Böblingen (DE); Thomas Alexander Schlebusch, Renningen (DE)

(73) Assignee: Kardion GmbH, Stuttgart (DE)

( * ) Notice: Subject to any disclaimer, the term of this patent is extended or adjusted under 35 U.S.C. 154(b) by 1081 days.

(21) Appl. No.: 17/057,044

(22) PCT Filed: May 30, 2019

(86) PCT No.: PCT/EP2019/064154
§ 371 (c)(1),
(2) Date: Jun. 1, 2021

(87) PCT Pub. No.: WO2019/229220
PCT Pub. Date: Dec. 5, 2019

(65) Prior Publication Data
US 2021/0290930 A1  Sep. 23, 2021

(30) Foreign Application Priority Data
May 30, 2018 (DE) ...................... 10 2018 208 538.2

(51) Int. Cl.
*A61M 60/135* (2021.01)
*A61M 60/174* (2021.01)
(Continued)

(52) U.S. Cl.
CPC ........ *A61M 60/135* (2021.01); *A61M 60/174* (2021.01); *A61M 60/237* (2021.01);
(Continued)

(58) Field of Classification Search
CPC .. A61M 2205/0238; A61M 2205/3331; A61M 2205/3368; A61M 2207/00;
(Continued)

(56) References Cited

U.S. PATENT DOCUMENTS 2,254,698 A   9/1941   Hansen, Jr.
2,310,923 A   2/1943   Bean
(Continued)

FOREIGN PATENT DOCUMENTS

AU   7993698    2/1999
AU   2002308409 12/2005
(Continued)

OTHER PUBLICATIONS

"ABMD—Taking a Closer Look at Impella ECP as the Pivotal Trial Gets Underway", Guggenheim, Press Release, Mar. 29, 2022, pp. 4.
(Continued)

*Primary Examiner* — Minh N Trinh
(74) *Attorney, Agent, or Firm* — Knobbe, Martens, Olson & Bear, LLP

(57) ABSTRACT

A method of manufacturing electrical tracks in a region of an intravascular blood pump is provided. The method can include providing an intravascular blood pump with a flow cannula including a spiral structure, a sensor and an electrical connection region, applying a conductor structure to a coatable material of the flow cannula, electrically connecting a first portion of the conductor track structure to the sensor and a second portion of the conductor track structure to the electrical connection region and closing the spiral structure using a flexible material where the flexible material can be silicone or polyurethane.

20 Claims, 5 Drawing Sheets

(51) Int. Cl.
*A61M 60/237* (2021.01)
*A61M 60/411* (2021.01)
*A61M 60/554* (2021.01)
*A61M 60/857* (2021.01)

(52) U.S. Cl.
CPC ........ *A61M 60/411* (2021.01); *A61M 60/554* (2021.01); *A61M 60/857* (2021.01); *A61M 2205/0238* (2013.01); *A61M 2205/3331* (2013.01); *A61M 2205/3368* (2013.01); *A61M 2207/00* (2013.01)

(58) Field of Classification Search
CPC .............. A61M 60/135; A61M 60/148; A61M 60/174; A61M 60/237
See application file for complete search history.

(56) References Cited

U.S. PATENT DOCUMENTS

| | | |
|---|---|---|
| 3,085,407 A | 4/1963 | Tomlinson |
| 3,088,323 A | 5/1963 | Welkowitz et al. |
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,023,562 A | 5/1977 | Hynecek et al. |
| 4,115,040 A | 9/1978 | Knorr |
| 4,471,252 A | 9/1984 | West |
| 4,522,194 A | 6/1985 | Normann |
| 4,559,952 A | 12/1985 | Angelsen et al. |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,781,525 A | 11/1988 | Hubbard et al. |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,045,051 A | 9/1991 | Milder et al. |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,269,811 A | 12/1993 | Hayes |
| 5,289,821 A | 3/1994 | Swartz |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,676,651 A | 10/1997 | Larson, Jr. et al. |
| 5,695,471 A | 12/1997 | Wampler |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,827,203 A | 10/1998 | Nita |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,904,708 A | 5/1999 | Goedeke |
| 5,911,685 A | 6/1999 | Siess et al. |
| 5,921,913 A | 7/1999 | Siess |
| 5,964,694 A | 10/1999 | Siess et al. |
| 5,980,465 A | 11/1999 | Elgas |
| 6,001,056 A | 12/1999 | Jassawalla et al. |
| 6,007,478 A | 12/1999 | Siess et al. |
| 6,018,208 A | 1/2000 | Maher et al. |
| 6,024,704 A | 2/2000 | Meador et al. |
| 6,050,975 A | 4/2000 | Poirier |
| 6,053,873 A | 4/2000 | Govari et al. |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,822 B1 | 1/2001 | Nix et al. |
| 6,176,848 B1 | 1/2001 | Rau et al. |
| 6,183,412 B1 | 2/2001 | Benkowsi et al. |
| 6,185,460 B1 | 2/2001 | Thompson |
| 6,186,665 B1 | 2/2001 | Maher et al. |
| 6,190,324 B1 | 2/2001 | Kieval et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,231,498 B1 | 5/2001 | Pfeiffer et al. |
| 6,245,007 B1 * | 6/2001 | Bedingham ......... A61M 60/812 600/16 |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,314,322 B1 | 11/2001 | Rosenberg |
| 6,351,048 B1 | 2/2002 | Schob et al. |
| 6,361,292 B1 | 3/2002 | Chang et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,445,956 B1 | 9/2002 | Laird et al. |
| 6,447,266 B2 | 9/2002 | Antaki et al. |
| 6,512,949 B1 | 1/2003 | Combs et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,540,659 B1 | 4/2003 | Milbocker |
| 6,544,216 B1 | 4/2003 | Sammler et al. |
| 6,561,975 B1 | 5/2003 | Pool et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,602,182 B1 | 8/2003 | Milbocker |
| 6,605,032 B2 | 8/2003 | Benkowsi et al. |
| 6,623,475 B1 | 9/2003 | Siess |
| 6,652,447 B2 | 11/2003 | Benkowsi et al. |
| 6,719,791 B1 | 4/2004 | Nüsser et al. |
| 6,731,976 B2 | 5/2004 | Penn et al. |
| 6,794,789 B2 | 9/2004 | Siess et al. |
| 6,841,910 B2 | 1/2005 | Gery |
| 6,879,126 B2 | 4/2005 | Paden et al. |

(56) References Cited

U.S. PATENT DOCUMENTS

| | | | |
|---|---|---|---|
| 6,912,423 B2* | 6/2005 | Ley | A61N 1/3752 |
| | | | 439/736 |
| 6,942,611 B2 | 9/2005 | Siess | |
| 6,949,066 B2 | 9/2005 | Bearnson et al. | |
| 6,969,345 B2 | 11/2005 | Jassawalla et al. | |
| 6,984,201 B2 | 1/2006 | Khaghani et al. | |
| 7,014,620 B2 | 3/2006 | Kim | |
| 7,022,100 B1 | 4/2006 | Aboul-Hosn et al. | |
| 7,024,244 B2 | 4/2006 | Muhlenberg et al. | |
| 7,027,875 B2 | 4/2006 | Siess et al. | |
| 7,011,620 B1 | 5/2006 | Siess | |
| 7,070,398 B2 | 7/2006 | Olsen et al. | |
| 7,070,555 B2 | 7/2006 | Siess | |
| 7,083,588 B1 | 8/2006 | Shmulewitz et al. | |
| 7,138,776 B1 | 11/2006 | Gauthier et al. | |
| 7,144,364 B2 | 12/2006 | Barbut et al. | |
| 7,160,243 B2 | 1/2007 | Medvedev | |
| 7,175,588 B2 | 2/2007 | Morello | |
| 7,177,681 B2 | 2/2007 | Xhu | |
| 7,238,151 B2 | 7/2007 | Frazier | |
| 7,241,257 B1 | 7/2007 | Ainsworth et al. | |
| 7,264,606 B2 | 9/2007 | Jarvik et al. | |
| 7,393,181 B2 | 7/2008 | McBride et al. | |
| 7,396,327 B2 | 7/2008 | Morello | |
| 7,462,019 B1 | 12/2008 | Allarie et al. | |
| 7,479,102 B2 | 1/2009 | Jarvik | |
| 7,502,648 B2 | 3/2009 | Okubo et al. | |
| 7,513,864 B2 | 4/2009 | Kantrowitz et al. | |
| 7,520,850 B2 | 4/2009 | Brockway | |
| 7,591,777 B2 | 9/2009 | LaRose | |
| 7,736,296 B2 | 6/2010 | Siess et al. | |
| 7,744,560 B2 | 6/2010 | Struble | |
| 7,762,941 B2 | 7/2010 | Jarvik | |
| 7,794,384 B2 | 9/2010 | Sugiura et al. | |
| 7,798,952 B2 | 9/2010 | Tansley et al. | |
| 7,819,916 B2 | 10/2010 | Yaegashi | |
| 7,841,976 B2 | 11/2010 | McBride et al. | |
| 7,850,593 B2 | 12/2010 | Vincent et al. | |
| 7,850,594 B2 | 12/2010 | Sutton et al. | |
| 7,856,335 B2 | 12/2010 | Morello et al. | |
| 7,862,501 B2 | 1/2011 | Woodward et al. | |
| 7,878,967 B1 | 2/2011 | Khanal | |
| 7,934,909 B2 | 2/2011 | Jenson | |
| 7,914,436 B1 | 3/2011 | Kung | |
| 7,951,062 B2 | 5/2011 | Morello | |
| 7,951,129 B2 | 5/2011 | Chinchoy | |
| 7,959,551 B2 | 6/2011 | Jarvik | |
| 7,963,905 B2 | 6/2011 | Salmonsen et al. | |
| 7,988,728 B2 | 8/2011 | Ayre | |
| 7,998,190 B2 | 8/2011 | Gharib et al. | |
| 8,012,079 B2 | 9/2011 | Delgado, III | |
| 8,075,472 B2 | 12/2011 | Zilbershlag et al. | |
| 8,088,059 B2 | 1/2012 | Jarvik | |
| 8,114,008 B2 | 2/2012 | Hidaka et al. | |
| 8,123,669 B2 | 2/2012 | Siess et al. | |
| RE43,299 E | 4/2012 | Siess | |
| 8,152,845 B2 | 4/2012 | Bourque | |
| 8,177,703 B2 | 5/2012 | Smith et al. | |
| 8,190,390 B2 | 5/2012 | Morello et al. | |
| 8,211,028 B2 | 7/2012 | Karamanoglu et al. | |
| 8,216,122 B2 | 7/2012 | Kung | |
| 8,303,482 B2 | 11/2012 | Schima et al. | |
| 8,323,173 B2 | 12/2012 | Benkowsi et al. | |
| 8,371,997 B2 | 2/2013 | Shifflette | |
| 8,376,926 B2 | 2/2013 | Benkowsi et al. | |
| 8,382,695 B1 | 2/2013 | Patel | |
| 8,388,565 B2 | 3/2013 | Shifflette | |
| 8,419,609 B2 | 4/2013 | Shambaugh, Jr. et al. | |
| 8,435,182 B1 | 5/2013 | Tamura | |
| 8,449,443 B2 | 5/2013 | Rodefeld et al. | |
| 8,449,444 B2 | 5/2013 | Poirier | |
| 8,480,555 B2 | 7/2013 | Kung | |
| 8,485,961 B2 | 7/2013 | Campbell et al. | |
| 8,512,012 B2 | 8/2013 | Akdis et al. | |
| 8,535,211 B2 | 9/2013 | Campbell et al. | |
| 8,545,380 B2 | 10/2013 | Farnan et al. | |
| 8,562,508 B2 | 10/2013 | Dague et al. | |
| 8,585,572 B2 | 11/2013 | Mehmanesh | |
| 8,591,393 B2 | 11/2013 | Walters et al. | |
| 8,591,538 B2 | 11/2013 | Gellman | |
| 8,591,539 B2 | 11/2013 | Gellman | |
| 8,594,790 B2 | 11/2013 | Kjellstrom et al. | |
| 8,597,170 B2 | 12/2013 | Walters et al. | |
| 8,617,239 B2 | 12/2013 | Reitan | |
| 8,622,949 B2 | 1/2014 | Zafirelis et al. | |
| 8,641,594 B2 | 2/2014 | LaRose et al. | |
| 8,657,733 B2 | 2/2014 | Ayre et al. | |
| 8,657,875 B2 | 2/2014 | Kung et al. | |
| 8,684,362 B2 | 4/2014 | Balsells et al. | |
| 8,684,904 B2 | 4/2014 | Campbell et al. | |
| 8,690,749 B1 | 4/2014 | Nunez | |
| 8,715,151 B2 | 5/2014 | Poirier | |
| 8,721,517 B2 | 5/2014 | Zeng et al. | |
| 8,727,959 B2 | 5/2014 | Reitan et al. | |
| 8,731,664 B2 | 5/2014 | Foster et al. | |
| 8,734,331 B2 | 5/2014 | Evans et al. | |
| 8,747,293 B2 | 6/2014 | Arndt et al. | |
| 8,814,933 B2 | 8/2014 | Siess | |
| 8,849,398 B2* | 9/2014 | Evans | A61M 60/405 |
| | | | 607/16 |
| 8,864,642 B2 | 10/2014 | Scheckel | |
| 8,864,643 B2 | 10/2014 | Reichenbach et al. | |
| 8,864,644 B2 | 10/2014 | Yomtov | |
| 8,876,685 B2 | 11/2014 | Crosby et al. | |
| 8,882,477 B2 | 11/2014 | Fritz, IV et al. | |
| 8,888,728 B2 | 11/2014 | Aboul-Hosn et al. | |
| 8,894,387 B2 | 11/2014 | White | |
| 8,897,873 B2 | 11/2014 | Schima et al. | |
| 8,900,060 B2 | 12/2014 | Liebing | |
| 8,900,115 B2 | 12/2014 | Bolling et al. | |
| 8,903,492 B2 | 12/2014 | Soykan et al. | |
| 8,932,246 B2 | 1/2015 | Ferrari | |
| 8,992,406 B2 | 3/2015 | Corbett | |
| 8,992,407 B2 | 3/2015 | Smith et al. | |
| 9,028,216 B2 | 5/2015 | Schumacher et al. | |
| 9,028,392 B2 | 5/2015 | Shifflette | |
| 9,033,863 B2 | 5/2015 | Jarvik | |
| 9,091,271 B2 | 7/2015 | Bourque | |
| 9,138,518 B2 | 9/2015 | Campbell et al. | |
| 9,144,638 B2 | 9/2015 | Zimmermann et al. | |
| 9,162,017 B2 | 10/2015 | Evans et al. | |
| 9,192,705 B2 | 11/2015 | Yanai et al. | |
| 9,199,020 B2 | 12/2015 | Siess | |
| 9,265,870 B2 | 2/2016 | Reichenbach et al. | |
| 9,297,735 B2 | 3/2016 | Graichen et al. | |
| 9,308,305 B2 | 4/2016 | Chen et al. | |
| 9,314,556 B2 | 4/2016 | Tuseth | |
| 9,327,067 B2 | 5/2016 | Zeng et al. | |
| 9,327,068 B2 | 5/2016 | Aboul-Hosn et al. | |
| 9,345,824 B2 | 5/2016 | Mohl et al. | |
| 9,370,613 B2 | 6/2016 | Hsu et al. | |
| 9,371,826 B2 | 6/2016 | Yanai et al. | |
| 9,381,286 B2 | 7/2016 | Spence et al. | |
| 9,421,311 B2 | 8/2016 | Tanner et al. | |
| 9,427,508 B2 | 8/2016 | Reyes et al. | |
| 9,433,713 B2 | 9/2016 | Corbett et al. | |
| 9,440,013 B2 | 9/2016 | Dowling et al. | |
| 9,474,840 B2 | 10/2016 | Siess | |
| 9,486,566 B2 | 11/2016 | Siess | |
| 9,492,601 B2 | 11/2016 | Casas et al. | |
| 9,511,179 B2 | 12/2016 | Casas et al. | |
| 9,533,084 B2 | 1/2017 | Siess et al. | |
| 9,539,378 B2 | 1/2017 | Tuseth | |
| 9,550,017 B2 | 1/2017 | Spanier et al. | |
| 9,555,173 B2 | 1/2017 | Spanier | |
| 9,555,175 B2 | 1/2017 | Bulent et al. | |
| 9,556,873 B2 | 1/2017 | Yanai et al. | |
| 9,561,313 B2 | 2/2017 | Taskin | |
| 9,566,374 B2 | 2/2017 | Spence et al. | |
| 9,579,433 B2 | 2/2017 | LaRose et al. | |
| 9,585,991 B2 | 3/2017 | Spence | |
| 9,592,397 B2 | 3/2017 | Hansen et al. | |
| 9,616,157 B2 | 4/2017 | Akdis | |
| 9,623,162 B2 | 4/2017 | Graham et al. | |

(56) References Cited

U.S. PATENT DOCUMENTS

| | | |
|---|---|---|
| 9,623,163 B1 | 4/2017 | Fischi |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,694,123 B2 | 7/2017 | Bourque et al. |
| 9,713,701 B2 | 7/2017 | Sarkar et al. |
| 9,731,058 B2 | 8/2017 | Siebenhaar et al. |
| 9,744,282 B2 | 8/2017 | Rosenberg et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,848,899 B2 | 12/2017 | Sliwa et al. |
| 9,849,223 B2 | 12/2017 | LaRose |
| 9,849,224 B2 | 12/2017 | Angwin et al. |
| 9,872,948 B2 | 1/2018 | Siess |
| 9,878,087 B2 * | 1/2018 | Richardson ......... A61M 1/3659 |
| 9,907,890 B2 | 3/2018 | Muller |
| 9,919,087 B2 | 3/2018 | Pfeffer et al. |
| 9,943,236 B2 | 4/2018 | Bennett et al. |
| 9,950,101 B2 | 4/2018 | Smith et al. |
| 9,950,102 B2 | 4/2018 | Spence et al. |
| 9,968,719 B2 | 5/2018 | Colella |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,413,651 B2 | 9/2019 | Yomtov et al. |
| 10,420,869 B2 | 9/2019 | Cornen |
| 10,426,879 B2 | 10/2019 | Farnan |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,322 B2 | 12/2019 | Karch |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,549,020 B2 | 2/2020 | Spence et al. |
| 10,557,475 B2 | 2/2020 | Roehn |
| 10,561,771 B2 | 2/2020 | Heilman et al. |
| 10,561,772 B2 | 2/2020 | Schumacher |
| 10,561,773 B2 | 2/2020 | Ferrari et al. |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,732,583 B2 | 8/2020 | Rudser |
| 10,814,053 B2 | 10/2020 | Throckmorton et al. |
| 10,857,273 B2 | 12/2020 | Hodges et al. |
| 10,857,275 B2 | 12/2020 | Granegger |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| RE48,649 E | 7/2021 | Siess |
| 11,058,863 B2 | 7/2021 | Demou |
| 11,058,865 B2 | 7/2021 | Fitzgerald et al. |
| 11,065,434 B2 | 7/2021 | Egler et al. |
| 11,067,085 B2 | 7/2021 | Granegger et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,120,908 B2 | 9/2021 | Agnello et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,131,968 B2 | 9/2021 | Rudser |
| 11,141,579 B2 | 10/2021 | Steingräber |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,185,682 B2 | 11/2021 | Farnan |
| 11,191,944 B2 | 12/2021 | Tuval et al. |
| 11,191,945 B2 | 12/2021 | Siess et al. |
| 11,197,618 B2 | 12/2021 | Edelman et al. |
| 11,197,989 B2 | 12/2021 | Arslan et al. |
| 11,202,901 B2 | 12/2021 | Barry |
| 11,217,344 B2 | 1/2022 | Agnello |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,139 B2 | 2/2022 | Kudlik |
| 11,235,140 B2 | 2/2022 | Siess et al. |
| 11,241,568 B2 | 2/2022 | Keenan et al. |
| 11,241,569 B2 | 2/2022 | Delgado, III |
| 11,241,572 B2 | 2/2022 | Dague et al. |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,299 B2 | 3/2022 | Wolman et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,285,310 B2 | 3/2022 | Curran et al. |
| 11,285,311 B2 | 3/2022 | Siess et al. |
| 11,291,824 B2 | 4/2022 | Schwammenthal et al. |
| 11,291,825 B2 | 4/2022 | Tuval et al. |

(56) References Cited

U.S. PATENT DOCUMENTS

| | | |
|---|---|---|
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| 11,316,679 B2 | 4/2022 | Agnello |
| D951,435 S | 5/2022 | Motomura et al. |
| 11,318,295 B2 | 5/2022 | Reyes et al. |
| 11,320,382 B2 | 5/2022 | Aikawa |
| 11,324,395 B2 | 5/2022 | Banik et al. |
| 11,324,940 B2 | 5/2022 | Earles et al. |
| 11,324,941 B2 | 5/2022 | Xu et al. |
| 11,331,082 B2 | 5/2022 | Itoh et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,337,724 B2 | 5/2022 | Masubuchi et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,358 B2 | 6/2022 | Nix et al. |
| 11,351,359 B2 | 6/2022 | Clifton et al. |
| 11,357,438 B2 | 6/2022 | Stewart et al. |
| 11,357,967 B2 | 6/2022 | Zeng et al. |
| 11,357,968 B2 | 6/2022 | El Katerji et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,443 B2 | 8/2022 | Hodges et al. |
| 11,413,444 B2 | 8/2022 | Nix et al. |
| 11,413,445 B2 | 8/2022 | Brown et al. |
| 11,413,446 B2 | 8/2022 | Siess et al. |
| 11,415,150 B2 | 8/2022 | Richert et al. |
| 11,420,041 B2 | 8/2022 | Karch |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,439,806 B2 | 9/2022 | Kimball et al. |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,521,723 B2 | 12/2022 | Liu et al. |
| 11,524,137 B2 | 12/2022 | Jahangir |
| 11,524,165 B2 | 12/2022 | Tan et al. |
| 11,527,322 B2 | 12/2022 | Agnello et al. |
| 11,529,062 B2 | 12/2022 | Moyer et al. |
| 11,534,596 B2 | 12/2022 | Schafir et al. |
| 11,554,260 B2 | 1/2023 | Reyes et al. |
| 11,565,103 B2 | 1/2023 | Farago et al. |
| 11,569,015 B2 | 1/2023 | Mourran et al. |
| 11,572,879 B2 | 2/2023 | Mohl |
| 11,574,741 B2 | 2/2023 | Tan et al. |
| 11,577,067 B2 | 2/2023 | Breidall et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,587,337 B2 | 2/2023 | Lemay et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,622,695 B1 | 4/2023 | Adriola et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,386 B2 | 5/2023 | Poirer |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,653,841 B2 | 5/2023 | Reyes et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,746 B2 | 6/2023 | Ferrari et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,676,718 B2 | 6/2023 | Agnello et al. |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,276 B2 | 6/2023 | Cros et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,707,617 B2 | 7/2023 | Reyes et al. |
| 11,708,833 B2 | 7/2023 | McBride et al. |
| 11,712,167 B2 | 8/2023 | Medvedev et al. |
| 11,744,987 B2 | 9/2023 | Siess et al. |
| 11,745,005 B2 | 9/2023 | Delgado, III |
| 11,746,906 B1 | 9/2023 | Balta et al. |

(56) References Cited

U.S. PATENT DOCUMENTS

| | | |
|---|---|---|
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| D1,001,145 S | 10/2023 | Lussier et al. |
| D1,001,146 S | 10/2023 | Lussier et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,550 B2 | 10/2023 | Siess et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,790,487 B2 | 10/2023 | Barbato et al. |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,813,443 B2 | 11/2023 | Hanson et al. |
| 11,813,444 B2 | 11/2023 | Siess et al. |
| 11,818,782 B2 | 11/2023 | Doudian et al. |
| 11,819,678 B2 | 11/2023 | Siess et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,833,278 B2 | 12/2023 | Siess et al. |
| 11,833,342 B2 | 12/2023 | Tanner et al. |
| 11,837,364 B2 | 12/2023 | Lee et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,857,743 B2 | 1/2024 | Fantuzzi et al. |
| 11,857,777 B2 | 1/2024 | Earles et al. |
| 11,864,878 B2 | 1/2024 | Duval et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| D1,014,552 S | 2/2024 | Lussier et al. |
| 11,890,082 B2 | 2/2024 | Cros et al. |
| 11,890,212 B2 | 2/2024 | Gilmartin et al. |
| 11,896,199 B2 | 2/2024 | Lent et al. |
| 11,896,482 B2 | 2/2024 | Delaloye et al. |
| 11,898,642 B2 | 2/2024 | Stanton et al. |
| 11,900,660 B2 | 2/2024 | Saito et al. |
| 11,903,657 B2 | 2/2024 | Geric et al. |
| 11,904,104 B2 | 2/2024 | Jahangir |
| 11,906,411 B2 | 2/2024 | Graichen et al. |
| 11,911,550 B2 | 2/2024 | Itamochi et al. |
| 11,911,579 B2 | 2/2024 | Tanner et al. |
| D1,017,634 S | 3/2024 | Lussier et al. |
| D1,017,699 S | 3/2024 | Moore et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,923,078 B2 | 3/2024 | Fallen et al. |
| 11,923,093 B2 | 3/2024 | Moffitt et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,938,311 B2 | 3/2024 | Corbett et al. |
| 11,944,805 B2 | 4/2024 | Stotz |
| 11,980,385 B2 | 5/2024 | Haselman |
| 11,986,274 B2 | 5/2024 | Edelman |
| 11,986,604 B2 | 5/2024 | Siess |
| 12,005,248 B2 | 6/2024 | Vogt et al. |
| 2001/0009645 A1 | 7/2001 | Noda |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2001/0041934 A1 | 11/2001 | Yamazaki et al. |
| 2002/0076322 A1 | 6/2002 | Maeda et al. |
| 2002/0147495 A1 | 10/2002 | Petroff |
| 2002/0151761 A1 | 10/2002 | Viole et al. |
| 2002/0153664 A1 | 10/2002 | Schroeder |
| 2003/0060685 A1 | 3/2003 | Houser |
| 2003/0069465 A1 | 4/2003 | Benkowski et al. |
| 2003/0091450 A1 | 5/2003 | Davis et al. |
| 2003/0100816 A1 | 5/2003 | Siess |
| 2003/0111800 A1 | 6/2003 | Kreutzer |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2004/0022640 A1 | 2/2004 | Siess et al. |
| 2004/0044266 A1 | 3/2004 | Siess et al. |
| 2004/0065143 A1 | 4/2004 | Husher |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0019167 A1 | 1/2005 | Nusser et al. |
| 2005/0085683 A1 | 4/2005 | Bolling et al. |
| 2005/0107658 A1 | 5/2005 | Brockway |
| 2005/0126268 A1 | 6/2005 | Ouriev et al. |
| 2005/0220636 A1 | 10/2005 | Henein et al. |
| 2005/0267322 A1 | 12/2005 | LaRose |
| 2006/0030809 A1 | 2/2006 | Barzilay et al. |
| 2006/0062672 A1 | 3/2006 | McBride et al. |
| 2006/0108901 A1 | 5/2006 | Mao-Chin |
| 2006/0122583 A1 | 6/2006 | Pesach et al. |
| 2006/0155158 A1 | 7/2006 | Aboul-Hosn |
| 2006/0196277 A1 | 9/2006 | Allen et al. |
| 2006/0224110 A1 | 10/2006 | Scott et al. |
| 2006/0229488 A1 | 10/2006 | Ayre et al. |
| 2006/0276682 A1 | 12/2006 | Bolling et al. |
| 2006/0287600 A1 | 12/2006 | McEowen |
| 2006/0287604 A1 | 12/2006 | Hickey |
| 2007/0004959 A1 | 1/2007 | Carrier et al. |
| 2007/0060787 A1 | 3/2007 | Peters et al. |
| 2007/0073352 A1 | 3/2007 | Euler et al. |
| 2007/0088214 A1 | 4/2007 | Shuros et al. |
| 2007/0142696 A1 | 6/2007 | Crosby et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2008/0015011 A1 | 1/2008 | Geistert et al. |
| 2008/0058925 A1 | 3/2008 | Cohen |
| 2008/0082005 A1 | 4/2008 | Stern et al. |
| 2008/0086027 A1 | 4/2008 | Siess et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |

(56) References Cited

U.S. PATENT DOCUMENTS

| | | |
|---|---|---|
| 2008/0108930 A1 | 5/2008 | Weitzel et al. |
| 2008/0114339 A1 | 5/2008 | McBride et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0292478 A1 | 11/2008 | Baykut et al. |
| 2008/0306328 A1 | 12/2008 | Ercolani |
| 2009/0004037 A1 | 1/2009 | Ito |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0112312 A1 | 4/2009 | Larose et al. |
| 2009/0131765 A1 | 5/2009 | Roschak et al. |
| 2009/0203957 A1 | 8/2009 | LaRose et al. |
| 2009/0204163 A1 | 8/2009 | Shuros et al. |
| 2009/0204205 A1 | 8/2009 | Larose et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0041939 A1 | 2/2010 | Siess |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0191035 A1 | 7/2010 | Kang et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0184224 A1 | 7/2011 | Garrigue |
| 2011/0184301 A1 | 7/2011 | Holmstrom |
| 2011/0218435 A1 | 9/2011 | Srinivasan et al. |
| 2011/0230821 A1 | 9/2011 | Babic |
| 2011/0237863 A1 | 9/2011 | Ricci et al. |
| 2011/0238172 A1 | 9/2011 | Akdis |
| 2012/0022645 A1 | 1/2012 | Burke |
| 2012/0035645 A1 | 2/2012 | Gross |
| 2012/0084024 A1 | 4/2012 | Norcross, Jr. |
| 2012/0088954 A1 | 4/2012 | Foster |
| 2012/0093628 A1 | 4/2012 | Liebing |
| 2012/0134793 A1 | 5/2012 | Wu et al. |
| 2012/0150089 A1 | 6/2012 | Penka et al. |
| 2012/0172655 A1 | 7/2012 | Campbell et al. |
| 2012/0178986 A1 | 7/2012 | Campbell et al. |
| 2012/0203476 A1 | 8/2012 | Dam |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0053623 A1 | 2/2013 | Evans |
| 2013/0066141 A1 | 3/2013 | Doerr et al. |
| 2013/0066142 A1 | 3/2013 | Doerr et al. |
| 2013/0072846 A1 | 3/2013 | Heide et al. |
| 2013/0085318 A1 | 4/2013 | Toellner |
| 2013/0116575 A1 | 5/2013 | Mickle et al. |
| 2013/0144379 A1 | 6/2013 | Najafi et al. |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0013852 A1 | 1/2014 | Brown et al. |
| 2014/0051908 A1 | 2/2014 | Khanal et al. |
| 2014/0079557 A1 | 3/2014 | LaRose et al. |
| 2014/0100414 A1 | 4/2014 | Tamez et al. |
| 2014/0107399 A1 | 4/2014 | Spence |
| 2014/0114202 A1 | 4/2014 | Hein et al. |
| 2014/0128659 A1 | 5/2014 | Heuring et al. |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0243688 A1 | 8/2014 | Caron et al. |
| 2014/0275720 A1 | 9/2014 | Ferrari |
| 2014/0275721 A1 | 9/2014 | Yanai et al. |
| 2014/0296677 A1 | 10/2014 | McEowen |
| 2014/0303426 A1 | 10/2014 | Kerkhoffs et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0032007 A1 | 1/2015 | Ottevanger et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0171694 A1 | 6/2015 | Dallas |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306290 A1 | 10/2015 | Rosenberg et al. |
| 2015/0306291 A1 | 10/2015 | Bonde et al. |
| 2015/0327921 A1 | 11/2015 | Govari |
| 2015/0335804 A1 | 11/2015 | Marseille et al. |
| 2015/0343179 A1 | 12/2015 | Schumacher et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0030649 A1 | 2/2016 | Zeng |
| 2016/0038663 A1 | 2/2016 | Taskin et al. |
| 2016/0045165 A1 | 2/2016 | Braido et al. |
| 2016/0045654 A1 | 2/2016 | Connor |
| 2016/0095968 A1 | 4/2016 | Rudser |
| 2016/0101230 A1 | 4/2016 | Ochsner et al. |
| 2016/0144089 A1 | 5/2016 | Woo et al. |
| 2016/0144166 A1 | 5/2016 | Decré et al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0250399 A1 | 9/2016 | Tiller et al. |
| 2016/0278856 A1 | 9/2016 | Panescu |
| 2016/0279311 A1 | 9/2016 | Cecere et al. |
| 2016/0338629 A1 | 11/2016 | Doerr |
| 2016/0367739 A1 | 12/2016 | Wiesener et al. |
| 2016/0375187 A1 | 12/2016 | Lee et al. |
| 2017/0010144 A1 | 1/2017 | Lenner et al. |
| 2017/0021069 A1 | 1/2017 | Hodges |
| 2017/0021070 A1 | 1/2017 | Petersen |
| 2017/0021074 A1 | 1/2017 | Opfermann et al. |
| 2017/0035952 A1 | 2/2017 | Muller |
| 2017/0049945 A1 | 2/2017 | Halvorsen et al. |
| 2017/0049947 A1 | 2/2017 | Corbett et al. |
| 2017/0080136 A1 | 3/2017 | Janeczek et al. |
| 2017/0086780 A1 | 3/2017 | Sokulin et al. |
| 2017/0087286 A1 | 3/2017 | Spanier et al. |
| 2017/0087288 A1 | 3/2017 | Groß-HardtTim et al. |
| 2017/0112985 A1 | 4/2017 | Yomtov |
| 2017/0128644 A1 | 5/2017 | Foster |
| 2017/0128646 A1 | 5/2017 | Karch |
| 2017/0136164 A1 | 5/2017 | Yeatts |

(56) References Cited

U.S. PATENT DOCUMENTS

| | | |
|---|---|---|
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0202575 A1 | 7/2017 | Stanfield et al. |
| 2017/0209633 A1 | 7/2017 | Cohen |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2017/0348470 A1 | 12/2017 | D'Ambrosio et al. |
| 2017/0354812 A1 | 12/2017 | Callaghan et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0099076 A1 | 4/2018 | LaRose |
| 2018/0110907 A1 | 4/2018 | Keenan et al. |
| 2018/0110910 A1 | 4/2018 | Rodemerk et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0250457 A1 | 9/2018 | Morello et al. |
| 2018/0256796 A1 | 9/2018 | Hansen |
| 2018/0256797 A1 | 9/2018 | Schenck et al. |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311423 A1 | 11/2018 | Zeng et al. |
| 2018/0316209 A1 | 11/2018 | Gliner |
| 2018/0318483 A1 | 11/2018 | Dague et al. |
| 2018/0318547 A1 | 11/2018 | Yokoyama |
| 2018/0326131 A1 | 11/2018 | Muller et al. |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0353667 A1 | 12/2018 | Moyer et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0001038 A1 | 1/2019 | Yomtov et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0192753 A1 | 6/2019 | Liu et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351118 A1 | 11/2019 | Graichen et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0060559 A1 | 2/2020 | Edelman et al. |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290087 A1 | 9/2021 | Schlebusch |
| 2021/0290929 A1 | 9/2021 | Stotz |
| 2021/0290930 A1* | 9/2021 | Kassel ............... A61M 60/554 |
| 2021/0290932 A1 | 9/2021 | Stotz |
| 2021/0290933 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |

(56) References Cited

U.S. PATENT DOCUMENTS

| | | |
|---|---|---|
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339002 A1 | 11/2021 | Schlebusch et al. |
| 2021/0339004 A1 | 11/2021 | Schlebusch et al. |
| 2021/0339005 A1 | 11/2021 | Stotz et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346677 A1 | 11/2021 | Baumbach et al. |
| 2021/0346678 A1 | 11/2021 | Baumbach et al. |
| 2021/0346680 A1 | 11/2021 | Vogt et al. |
| 2021/0378523 A1 | 12/2021 | Budde |
| 2021/0379352 A1 | 12/2021 | Schlebusch et al. |
| 2021/0379355 A1 | 12/2021 | Schuelke et al. |
| 2021/0379359 A1 | 12/2021 | Schellenberg |
| 2021/0379360 A1 | 12/2021 | Schellenberg |
| 2021/0384812 A1 | 12/2021 | Vollmer et al. |
| 2021/0393944 A1 | 12/2021 | Wenning |
| 2022/0008714 A1 | 1/2022 | Stotz |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072296 A1 | 3/2022 | Mori |
| 2022/0072297 A1 | 3/2022 | Tuval et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0407403 A1 | 12/2022 | Vogt et al. |
| 2023/0001178 A1 | 1/2023 | Corbett et al. |
| 2023/0173250 A1 | 6/2023 | Stigloher |
| 2023/0191141 A1 | 6/2023 | Wenning et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0011808 A1 | 1/2024 | Winzer et al. |
| 2024/0074828 A1 | 3/2024 | Wenning |
| 2024/0075277 A1 | 3/2024 | Schellenberg |
| 2024/0102475 A1 | 3/2024 | Schuelke et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 664 835 | 2/2008 |
| CA | 2 796 357 | 10/2011 |
| CA | 3 122 415 | 7/2020 |
| CA | 2 947 984 | 11/2022 |
| CN | 1192351 A | 9/1998 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1661338 A | 8/2005 |
| CN | 1833736 A | 9/2006 |
| CN | 200977306 | 11/2007 |
| CN | 101112628 | 1/2008 |
| CN | 101128168 | 2/2008 |
| CN | 101208045 | 6/2008 |
| CN | 101214158 | 7/2008 |
| CN | 201150675 | 11/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201618200 | 11/2010 |
| CN | 201658687 | 12/2010 |
| CN | 201710717 | 1/2011 |
| CN | 201894758 | 7/2011 |
| CN | 102421372 | 4/2012 |
| CN | 102475923 | 5/2012 |
| CN | 102545538 | 7/2012 |
| CN | 202314596 | 7/2012 |
| CN | 102743801 | 10/2012 |
| CN | 102803923 | 11/2012 |
| CN | 103143072 | 6/2013 |
| CN | 103328018 | 9/2013 |
| CN | 103845766 | 6/2014 |
| CN | 103857326 | 6/2014 |
| CN | 103861162 | 6/2014 |
| CN | 103957957 | 7/2014 |
| CN | 203842087 | 9/2014 |
| CN | 104105449 | 10/2014 |
| CN | 104188687 | 12/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 106104229 | 11/2016 |
| CN | 106333707 | 1/2017 |
| CN | 104888293 | 3/2017 |
| CN | 106512117 | 3/2017 |
| CN | 206007680 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107530479 | 1/2018 |
| CN | 107632167 | 1/2018 |
| CN | 107921187 | 4/2018 |
| CN | 105498002 | 6/2018 |
| CN | 106310410 | 7/2018 |
| CN | 109939282 | 6/2019 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 26 24 058 | 12/1977 |
| DE | 3 545 214 | 7/1986 |
| DE | 195 20 920 | 12/1995 |
| DE | 195 46 336 | 5/1997 |
| DE | 695 01 834 | 10/1998 |
| DE | 198 54 724 | 5/1999 |
| DE | 198 21 307 | 10/1999 |

(56) References Cited

FOREIGN PATENT DOCUMENTS

| | | |
|---|---|---|
| DE | 199 10 872 | 10/1999 |
| DE | 199 56 380 | 11/1999 |
| DE | 100 59 714 | 5/2002 |
| DE | 100 60 275 | 6/2002 |
| DE | 101 55 011 | 11/2005 |
| DE | 601 19 592 | 9/2006 |
| DE | 20 2005 020 288 | 6/2007 |
| DE | 10 2006 001 180 | 9/2007 |
| DE | 10 2008 060 357 | 6/2010 |
| DE | 10 2009 007 216 | 8/2010 |
| DE | 10 2009 011 726 | 9/2010 |
| DE | 10 2009 025 464 | 1/2011 |
| DE | 10 2009 039 658 | 3/2011 |
| DE | 10 2009 047 845 | 3/2011 |
| DE | 20 2009 018 416 | 8/2011 |
| DE | 10 2011 106 142 | 12/2012 |
| DE | 20 2011 110 389 | 9/2013 |
| DE | 10 2012 022 456 | 5/2014 |
| DE | 10 2013 007 562 | 11/2014 |
| DE | 10 2015 004 177 | 10/2015 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 20 2015 009 422 | 7/2017 |
| DE | 10 2012 207 042 | 9/2017 |
| DE | 10 2016 013 334 | 4/2018 |
| DE | 10 2017 212 193 | 1/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 003 151 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 794 411 | 9/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 062 959 | 12/2000 |
| EP | 1 339 443 | 11/2001 |
| EP | 1 186 873 | 3/2002 |
| EP | 1 011 803 | 9/2004 |
| EP | 1 475 880 | 11/2004 |
| EP | 1 169 072 | 5/2005 |
| EP | 1 176 999 | 7/2005 |
| EP | 1 354 606 | 6/2006 |
| EP | 1 801 420 | 6/2007 |
| EP | 2 009 233 | 12/2008 |
| EP | 2 098 746 | 9/2009 |
| EP | 2 143 385 | 1/2010 |
| EP | 2 175 770 | 4/2010 |
| EP | 2 403 109 | 1/2012 |
| EP | 2 187 807 | 6/2012 |
| EP | 2 570 143 | 3/2013 |
| EP | 2 401 003 | 10/2013 |
| EP | 3 326 567 | 10/2014 |
| EP | 1 871 441 | 11/2014 |
| EP | 1 898 971 | 3/2015 |
| EP | 2 859 911 | 4/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 2 213 227 | 8/2016 |
| EP | 2 835 141 | 8/2016 |
| EP | 3 069 739 | 9/2016 |
| EP | 3 088 016 | 11/2016 |
| EP | 3 127 562 | 2/2017 |
| EP | 2 585 129 | 3/2017 |
| EP | 3 222 301 | 9/2017 |
| EP | 3 222 302 | 9/2017 |
| EP | 2 945 661 | 11/2017 |
| EP | 2 136 861 | 12/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 456 367 | 3/2019 |
| EP | 3 119 451 | 6/2019 |
| EP | 3 389 738 | 8/2019 |
| EP | 3 542 835 | 9/2019 |
| EP | 3 542 836 | 9/2019 |
| EP | 3 062 877 | 12/2019 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 142 722 | 12/2020 |
| EP | 3 579 894 | 12/2020 |
| EP | 3 753 594 | 12/2020 |
| EP | 3 188 769 | 1/2021 |
| EP | 3 357 523 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 490 628 | 2/2021 |
| EP | 3 113 806 | 3/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 131 600 | 6/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 579 904 | 11/2021 |
| EP | 2 628 493 | 12/2021 |
| EP | 3 164 168 | 12/2021 |
| EP | 3 344 129 | 12/2021 |
| EP | 3 556 409 | 1/2022 |
| EP | 3 624 868 | 1/2022 |
| EP | 3 624 867 | 3/2022 |
| EP | 3 651 822 | 3/2022 |
| EP | 3 689 389 | 3/2022 |
| EP | 3 697 464 | 3/2022 |
| EP | 3 737 436 | 3/2022 |
| EP | 3 972 661 | 3/2022 |

(56) References Cited

FOREIGN PATENT DOCUMENTS

| | | |
|---|---|---|
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 2 999 400 | 8/2022 |
| EP | 3 711 788 | 8/2022 |
| EP | 3 899 994 | 8/2022 |
| EP | 3 487 550 | 9/2022 |
| EP | 3 606 575 | 9/2022 |
| EP | 3 694 573 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 370 797 | 1/2023 |
| EP | 3 393 542 | 1/2023 |
| EP | 3 597 231 | 1/2023 |
| EP | 3 656 292 | 1/2023 |
| EP | 3 668 562 | 1/2023 |
| EP | 3 768 345 | 1/2023 |
| EP | 3 856 275 | 1/2023 |
| EP | 2 868 332 | 2/2023 |
| EP | 3 003 420 | 2/2023 |
| EP | 3 397 299 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 685 562 | 5/2023 |
| EP | 3 544 649 | 6/2023 |
| EP | 3 634 528 | 6/2023 |
| EP | 3 397 298 | 7/2023 |
| EP | 3 809 959 | 7/2023 |
| EP | 3 912 673 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 3 554 576 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 781 027 | 11/2023 |
| EP | 3 808 390 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 566 636 | 2/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| ES | 2 913 485 | 6/2022 |
| FR | 1458525 | 3/1966 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | S59-080229 | 5/1984 |
| JP | 59-119788 | 8/1984 |
| JP | S61-500059 | 1/1986 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | 2-79738 | 3/1990 |
| JP | H02-234750 | 9/1990 |
| JP | H04-176471 | 6/1992 |
| JP | H04-108384 | 9/1992 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | 2888609 | 5/1999 |
| JP | 2889384 | 5/1999 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-515375 | 9/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2004-278375 | 10/2004 |
| JP | 2005-028137 | 2/2005 |
| JP | 2005-507039 | 3/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2008-516654 | 5/2008 |

(56) References Cited

FOREIGN PATENT DOCUMENTS

| | | |
|---|---|---|
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2010-258181 | 11/2010 |
| JP | 2010-534080 | 11/2010 |
| JP | 2012-520157 | 9/2012 |
| JP | 2013-013216 | 1/2013 |
| JP | 2013-519497 | 5/2013 |
| JP | 2013-128792 | 7/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2016-532500 | 10/2016 |
| JP | 2017-500932 | 1/2017 |
| JP | 6063151 | 1/2017 |
| JP | 2017-176719 | 10/2017 |
| JP | 2017-532084 | 11/2017 |
| JP | 6267625 | 1/2018 |
| JP | 2018-057878 | 4/2018 |
| JP | 2019-523110 | 8/2019 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 92/015239 | 9/1992 |
| WO | WO 94/009835 | 5/1994 |
| WO | WO 97/037696 | 10/1997 |
| WO | WO 97/039785 | 10/1997 |
| WO | WO 98/043688 | 10/1998 |
| WO | WO 99/049912 | 10/1999 |
| WO | WO 00/033047 | 6/2000 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2010/142286 | 12/2010 |
| WO | WO 2010/143272 | 12/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2012/112378 | 8/2012 |
| WO | WO 2013/037380 | 3/2013 |
| WO | WO 2013/120957 | 8/2013 |
| WO | WO 2013/160443 | 10/2013 |
| WO | WO 2013/167432 | 11/2013 |
| WO | WO 2013/173239 | 11/2013 |
| WO | WO 2014/042925 | 3/2014 |
| WO | WO 2014/141284 | 9/2014 |
| WO | WO 2014/165635 | 10/2014 |
| WO | WO 2015/039605 | 3/2015 |
| WO | WO 2015/063281 | 5/2015 |
| WO | WO 2015/085076 | 6/2015 |
| WO | WO 2015/085220 | 6/2015 |
| WO | WO 2015/109028 | 7/2015 |
| WO | WO 2015/172173 | 11/2015 |
| WO | WO 2015/175718 | 11/2015 |
| WO | WO 2016/001284 | 1/2016 |
| WO | WO 2016/028644 | 2/2016 |
| WO | WO 2016/066180 | 5/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/032751 | 3/2017 |
| WO | WO 2017/053988 | 3/2017 |
| WO | WO 2017/060257 | 4/2017 |
| WO | WO 2017/066257 | 4/2017 |
| WO | WO 2017/106190 | 6/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2017/214118 | 12/2017 |
| WO | WO 2018/007120 | 1/2018 |
| WO | WO 2018/036927 | 3/2018 |
| WO | WO 2018/048800 | 3/2018 |
| WO | WO 2018/088939 | 3/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/035804 | 2/2019 |
| WO | WO 2019/038343 | 2/2019 |
| WO | WO 2019/057636 | 3/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2019/193604 | 10/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234145 | 12/2019 |

(56) References Cited

FOREIGN PATENT DOCUMENTS

| | | |
|---|---|---|
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030686 | 2/2020 |
| WO | WO 2020/030700 | 2/2020 |
| WO | WO 2020/030706 | 2/2020 |
| WO | WO 2020/064707 | 4/2020 |
| WO | WO 2020/064911 | 4/2020 |
| WO | WO 2020/073047 | 4/2020 |
| WO | WO 2020/089429 | 5/2020 |
| WO | WO 2020/132211 | 6/2020 |
| WO | WO 2020/187797 | 9/2020 |
| WO | WO 2020/198280 | 10/2020 |
| WO | WO 2020/219430 | 10/2020 |
| WO | WO 2020/234785 | 11/2020 |
| WO | WO 2020/242881 | 12/2020 |
| WO | WO 2020/243756 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/074136 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |

OTHER PUBLICATIONS

Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.
Atkinson et al., "Pulse-Doppler Ultrasound and Its Clinical Application", The Yale Journal of Biology and Medicine, 1977, vol. 50, pp. 367-373.
Leguy et al., "Assessment of Blood Volume Flow in Slightly Curved Arteries from a Single Velocity Profile", Journal of Biomechanics, 2009, pp. 1664-1672.
Lombardi et al., "Flow Rate Profiler: an instrument to measure blood velocity profiles", Ultrasonics, 2001, vol. 39, pp. 143-150.
Mushi et al., "Identification of Fluidic Element Models to Simulate the Short-Term Baroreflex",|Proceedings of the 45th IEEE Conference on Decision & Control, San Diego, CA, Dec. 13-15, 2006, pp. 6.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
"Understanding Hot-Wire Anemometry", Advanced Thermal Solutions, Inc., 2007, pp. 13-17.
Vieli, A., "Doppler Flow Determination", BJA: British Journal of Anaesthesia, 1988, vol. 60, pp. 107S-112S.
Yuanyuan et al., "Characteristics Analysis for Doppler Ultrasound Blood Flow Signals", China Medical Device Information, 5(1), Feb. 28, 1999, pp. 36-42.
Zhang, Dabiao et al., "Design of Microwave Velocity and Distance Monitor System", Instrument Technique and Sensor, Hebei Normal University, Apr. 25, 2004, pp. 3.
Hertz Ph.D et aL, "Ultrasonic Engineering in Heart Diagnosis", The American Journal of Cardiology, Jan. 1967, vol. 19, No. 1, pp. 6-17.
International Search Report and Written Opinion received in PCT Application No. PCT/EP2019/064154, dated Sep. 6, 2019 in 8 pages.
International Preliminary Report on Patentability and Written Opinion received in PCT Application No. PCT/EP2019/064154, dated Dec. 10, 2020 in 7 pages.
Kong et al., "A Stein Equation Approach for Solutions to the Diophantine Equations," 2010 Chinese Control and Decision Conference, Xuzhou, May 26, 2010, pp. 3024-3028.
Koseli et al., "Online Viscosity Measurement of Complex Solutions Using Ultrasound Doppler Velocimetry", Turk J Chem, Jan. 2006, vol. 30, pp. 297-305.
McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.
Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.
Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.
Escudeiro et al., "Tribological behavior of uncoated and DLC-coated CoCr and Ti-alloys in contact with UHMWPE and PEEK counterbodies;" Tribology International, vol. 89, 2015, pp. 97-104.
Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
Neale, Michael J., "The Tribology Handbook;" 1999, Butterworth-Heinemann, Second Edition, pp. 582.
Park et al., "A Novel Electrical Potential Sensing Method for in Vitro Stent Fracture Monitoring and Detection", Jan. 1, 2011, vol. 21, No. 4, pp. 213-222.
Sak et al., "Influence of polyetheretherketone coatings on the Ti-13Nb-13Zr titanium alloy's bio-tribological properties and corrosion resistance;" Materials Science and Engineering: C, vol. 63, 2016, pp. 52-61.

* cited by examiner

METHOD OF MANUFACTURING ELECTRICAL CONDUCTOR TRACKS IN A REGION OF AN INTRAVASCULAR BLOOD PUMP

BACKGROUND

Field

The present invention relates to an intravascular blood pump, which can in particular be used as a cardiac support system. The invention further relates to a method for producing electrical conductor tracks in such a blood pump.

Description of the Related Art

So-called left ventricular assist devices (LVAD) are a known option for supporting the pumping function of the heart. These are surgically implantable mechanical pumps that support the heart. By continuously pumping blood, the blood is pumped from the left ventricle into the aorta, so that enough oxygen-rich blood can circulate in the body in a heart failure patient. So-called balloon pumps are known for this purpose. Moreover, rotary blood pumps have already been developed that can in particular also be inserted into the left ventricle and the aorta in a minimally invasive manner. The right side of the heart, for example, can also be supported in a corresponding manner. Such systems place high demands on overall size. The necessary small dimensions are achieved, for example, by reducing the wall thicknesses to a minimum. However, the integration of active electronic components or sensors in general with suitable connections is difficult. The international patent application WO 2013/160443 A1 describes an intravascular rotary blood pump in which an optical pressure sensor is integrated into the system, wherein the optical connection via optical fibers is implemented in a complex manner using neutral fibers along the flow cannula of the blood pump.

SUMMARY

The object of the invention is to provide an improved intravascular blood pump and a method for producing such a blood pump. One object of the invention is in particular to create an intravascular blood pump, which [enables] the operation of electrical components, in particular the operation of sensors disposed, for example, in the region of a tip of the blood pump, and/or evaluation electronics disposed in said location.

This object is achieved by an intravascular blood pump having the features described herein. Such a blood pump can be produced with the method described herein.

The invention provides an intravascular blood pump, which is in particular based on the rotary pump principle, that can in particular be used as a cardiac support system. The blood pump comprises a tip, a first region with at least one blood through-opening, a flow cannula, a second region with at least one blood through-opening, a motor-operated pump device and a conducting cable for the electrical supply and control of the system. The blood pump is characterized in that at least one electrical conductor track is provided by a surface coating structure at least in the region of the flow cannula. Electrical connections and/or sensors can be realized via the electrical conductor track(s). At least one electronic component can thus be disposed in the region of the tip, in particular one or more active electronic components, for the electrical connection of which the at least one electrical conductor track is used. Such electrical conductor tracks make it possible to reduce the thickness of the electrical connecting lines to a minimum in a particularly advantageous manner. This satisfies the need for small size for such systems. Such surface coating structures in particular make it possible to bridge the region of the flow cannula. However, other regions of the blood pump can also be bridged; for example the regions of the blood through-openings and the pump device or parts thereof. Electronic components in the tip of the system can thus be electrically connected to further away regions of the system, in particular to the conducting cable, so that power transmission and/or data transmission from or to external control devices and/or evaluation devices, for example, is possible. The invention permits a very advantageous electrical contacting of electronic components in the tip or also at another position, whereby the implementation of the electrical contacting or connection to the conducting cable can be very thin and space-saving and, at the same time, very firm, stable and reliable due to the electrical surface functionalization. The assembly process required for this can be realized in a cost-effective manner.

The electronic components in the region of the tip can in particular be sensors, for example pressure sensors, flow measuring sensors, temperature sensors, etc. Optical sensors, acceleration or rotation rate sensors and acoustic sensors (microphones), for example, are possible as well. Any sensors or other electronic components and electrode surfaces that are suitable for medical monitoring of the patient and/or the function of the intravascular blood pump and/or for controlling the blood pump can be used.

As an alternative or in addition to an electrical connection of electronic components via the conductor tracks, sensors can be realized using the conductor tracks themselves, for example strain sensors and/or breakage sensors and/or temperature sensors. In this way, sensors can be integrated into the surface structure in a very advantageous manner. The use of exposed electrodes for recording electrical excitation signals or for performing an electrical impedance measurement is possible as well. Such sensors can be realized by sensor regions within the surface coating structure which comprise meandering conductor tracks. The conductor tracks in the sensor region(s) can also be made of a different material than the conductor tracks outside the sensor regions. The conductor tracks in a sensor region can be made of platinum, for example, which allows the sensor region to be used as a temperature sensor. Such sensor regions can furthermore also be used as electrical sensors, so that the sensors can be used for dielectric characterization of the surrounding blood, for example. The coupling can be conductive or capacitive, comparable to an impedance spectroscopy. It is also possible to integrate a thin surface wave sensor, for example as a thin ceramic disc, for example for determining the blood viscosity.

The flow cannula of the intravascular blood pump preferably comprises one or more coatable materials. A hose guide made of a coatable material can in particular be provided. The surface coating structure is applied to the coatable material or materials to realize the electrical conductor tracks. As a general rule, it is useful for the flow cannula to be flexible. For this purpose, the hose guide can, for example, be equipped with a flexible skeletal structure, for example a spiral structure. Other options include zigzag or wave structures. The flexible structure (e.g. the spiral structure) is expediently designed such that there is a continuous web structure on which the electrical conductor tracks are held. Such flexible structures are particularly advantageously at least partially made of the coatable material. Metallic materials, for example titanium and/or stainless steel, can be used as coatable materials. Nickel-titanium alloys (NiTiNoI), which are already used in medical technology due to their particularly advantageous properties, are particularly preferred. In addition to their advantages in terms of their deformation properties, nickel-titanium alloys also have the advantage of being directly coatable. Other suitable coatable materials are, for example, glass and/or ceramic.

The surface coating structure can preferably have a multilayer structure, for example a two-layer structure, whereby the lower layer in the space between two conductor structures can be used for metallizing a further conductor layer, so that multiple conductor track layers are nested inside one another. On the one hand, this allows the overall conductor width to be reduced. On the other hand, the layer thickness of the conductor structure as a whole is reduced.

For electrical contacting of the conductor tracks it is preferable that electrical contact pads are provided. The contact pads can be disposed at the end of the flow cannula, for example, opposite the tip of the system.

The invention further involves a method for producing electrical conductor tracks at least in the region of a flow cannula of an intravascular blood pump, wherein, concerning this blood pump, reference is made to the above description. The electrical conductor tracks are produced using a surface coating, in particular using surface lithographic techniques. First and foremost, optical lithographic methods (e.g. UV lithography) can be used. Flat 2D wafer processes can be used on cylindrical bodies, for example, so that conventional lithography processes can in principle be used by adapting the exposure devices. Photolithographic methods, in particular three-dimensional UV photolithographic methods, are particularly suitable. Magnetron sputtering and, if necessary, wet chemical etching methods can in particular be used to produce the surface structuring.

In a preferred embodiment of the method, after a possibly necessary initial cleaning and surface activation of the material to be coated, an insulating base layer can first be applied to the coatable material. This can be an oxide layer that is applied by sputtering, for example, or a polyimide. A photoresist is then applied and structured in accordance with the conductor tracks to be applied. For this purpose, a lithography mask is expediently applied, for example made of chrome-coated quartz substrate, before the photoresist is exposed and developed. The metallic conductor track structure is then applied by sputtering. For reasons of biocompatibility, gold is preferably used as the material for the conductor tracks. The photoresist is then removed. Finally, an electrically insulating and preferably biocompatible surface is applied. This too can again be done by sputtering oxide, for example, or by applying polyimide or parylene or something else. The layer thickness of the resulting sputtered surfaces is preferably in a range of several hundred nanometers.

In particular for applications that require a high conductivity of the conductor track structures, a conductor track structure with an increased layer thickness (for example several micrometers) can be provided using the design variant of the method described in the following. For this purpose, an in principle complete conductive surface coating is produced first. This is windowed by a structured photoresist and the exposed windows are then galvanically thickened. Specifically, in this variant, after a possibly necessary initial cleaning and surface activation, an insulating base layer is applied first, for example an oxide layer by sputtering or a base layer of polyimide. Then an initial metallic conductor layer (e.g. gold) is applied. A photoresist is applied to the initial conductor layer and structured in accordance with the conductor tracks to be applied.

The exposed metallic conductor tracks or the exposed windows are then thickened using a wet chemical electroplating process so that the desired conductivity can be produced in the exposed metal structures. The photoresist is removed. To remove the initial metal conductor layer outside the conductor track structures, the surface is etched so that the electrical conductor track structures are exposed. Lastly, an electrically insulating and preferably biocompatible surface is applied, for example by sputtering oxide or by applying polyimide or parylene or other materials.

In addition to the surface structuring for producing the conductor tracks, the process preferably also includes the structuring of the pipe material, in which a web structure is produced on which the conductor tracks are held (for example a spiral structure). This structuring can occur before or after the production of the conductor tracks. Finally, the windows of the web structure are closed with silicone or polyurethane, for example.

Further features and advantages of the invention emerge from the following description of design examples in conjunction with the drawing. The individual features can be realized individually or in combination with one another.

BRIEF DESCRIPTION OF THE DRAWINGS

Advantageous embodiments of the invention are shown schematically in the drawings and are described in the following.

The figures show.

DETAILED DESCRIPTION

Figure 1:
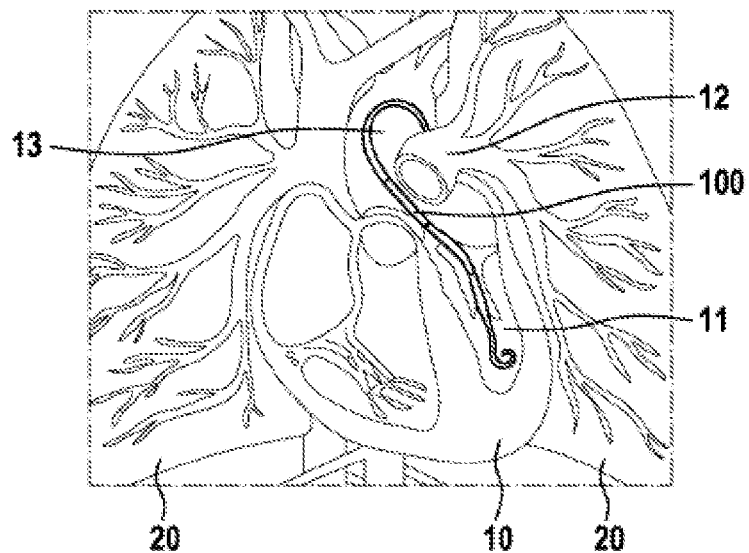
FIG. 1 a sectional view of a human heart and lung with an inserted intravascular blood pump.

FIG. 1 shows a human heart 10 and the surrounding lungs 20, wherein an intravascular blood pump 100 is inserted in the left ventricle 11. Pumping the blood pump 100 supports the pumping function of the heart 10 by moving oxygen-rich blood coming into the left ventricle 11 from the pulmonary vein 12 into the aorta 13. The intravascular blood pump can be designed for continuous pumping, for example, or the pump is based on a pulsatile system, for example, in which the pump speed is modulated.

Figure 2:
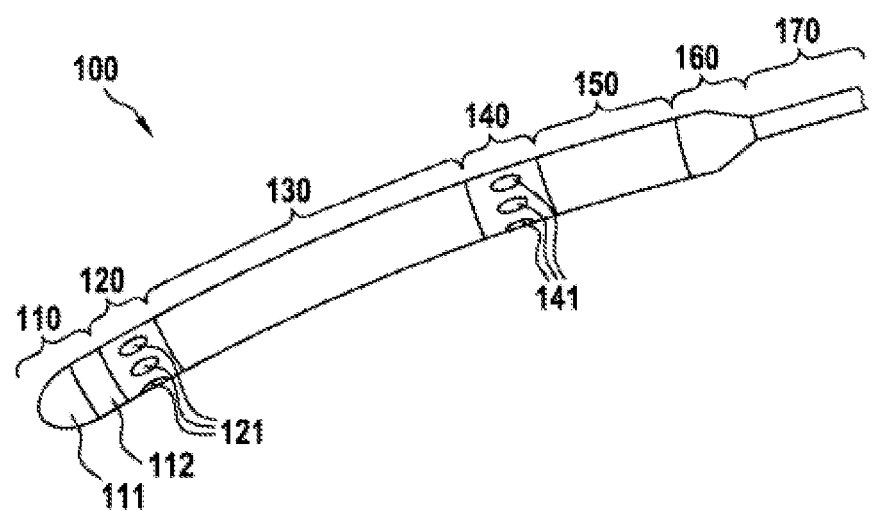
FIG. 2 components of an intravascular blood pump (LVAD system)

FIG. 2 schematically shows the components of an intravascular blood pump 100 that is equipped according to the invention with a surface coating structure for the formation of electrical conductor tracks. The blood pump 100 comprises a tip 110, wherein one or more electronic components 112, in particular sensors, can be provided in a region within the tip 110. The tip is closed by a slidable cap 111. A first region 120 (inlet cage) with blood through-openings 121 adjoins the tip 110. Blood can be drawn into the blood pump, for example from the left ventricle, through the blood through-openings 121. This is adjoined by a flow cannula 130 and a second region 140 (impeller cage) having further blood through-openings 141. This is adjoined by region 150 for a motor-operated pump device. Inside the region 140 there is a rotor (impeller), for example, that is operated via the pump device 150, so that the pumped blood can exit through the blood through-openings 141. The pump device 150 is adjoined by a back end 160, via which the electrical connection is made. A supply cable 170 is provided for electrical supply and control. The motor-operated pump device is preferably a rotary pump (flow machine), wherein a reversal of the conveying direction can also be provided if necessary.

The surface coating structure according to the invention allows sensors or sensor regions, for example breakage sensors or strain sensors or temperature sensors, to be realized, in particular in the region of the flow cannula. The surface coating structures can also be used to electrically connect any existing electronic components 112 of the tip 110 to the supply cable 170. This allows the length of the flow cannula 130 in particular, but also the regions 120 and 140 and the region with the motor-operated pump device 150, to be bridged. Different components can be combined and realized as one structural element. For example, the first region 120 can be combined with the flow cannula 130 to one structural element, which can then very advantageously be equipped with the surface coating structure according to the invention for the formation of conductor tracks.

Figure 3:
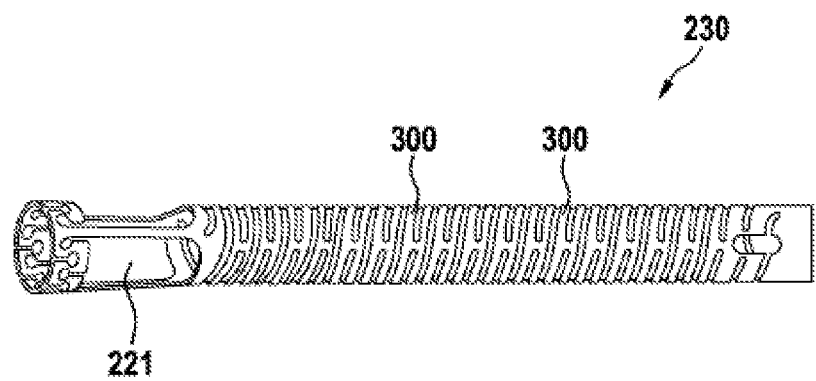
FIG. 3 an isometric illustration of a flexible hose guide of the flow cannula of an intravascular blood pump.

FIG. 3 shows a combined configuration of the first region with blood through-openings 221, which is directly adjoined by the flow cannula 230. The flow cannula 230 is advantageously realized as a flexible inlet hose or as a flexible hose guide. In this example, the flexible flow cannula 230 is realized by a spiral-shaped structure formed by circumferential windowed webs 300. A laser-structured tube made of NiTiNoI material, for example, can be provided as the coatable material for this purpose. On the right side of the laser structured tube there is an elongated opening, which is provided for the passage of a guide wire in a per se known manner during the implantation process. The skeleton or web structures 300 of the NiTiNoI material are electrically functionalized by surface coating for the formation of the conductor tracks, whereby the conductor tracks can in particular be used for electrically connecting electronic components and/or for the formation of sensors. The spiral structure of the NiTiNoI tube can be produced by laser structuring. The exposed windows of the laser structured form can be closed by flexible materials, for example by silicone or polyurethane. The flexibility of the hose guide can also be achieved with other structures, for example by zigzag or wave patterns. The surface coating structure as such can be applied according to the method already described above. In this context, reference is also made to an article by Bechtold et al. (Biomed Microdevices, 2016 December; 18(6): 106) and an article by Lima de Miranda et al. (Rev. Sci. Instrum., 2009 January; 80(1): 015103), whereby these articles deal with surface structuring in general. Bechtold et al. describe the coating of thin films made of a nickel-titanium alloy to form insulated electrodes on the outer surface. Lima de Miranda et al. describe a rotational UV lithography for cylindrical geometries. The laser structuring of the NiTiNoI tube to form the spiral structure, for example, can take place before or after the electrical functionalization.

Figure 4:
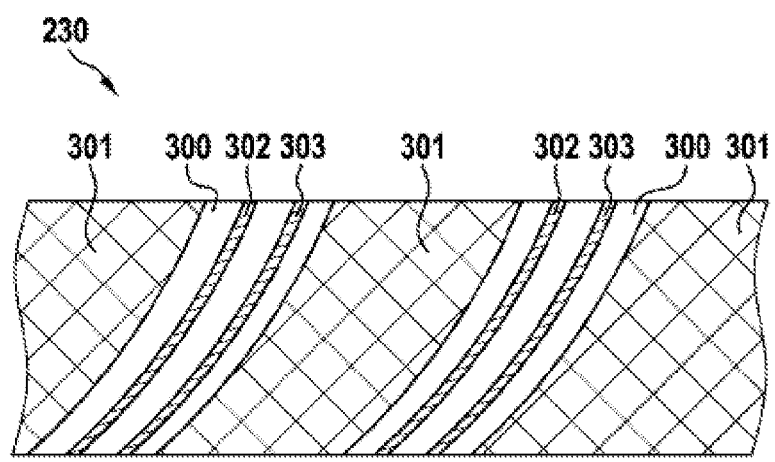
FIG. 4 a detail view of the hose guide of a flow cannula having a surface coating structure according to the invention for the formation of conductor tracks.

FIG. 4 shows a detail view of the resulting exemplary conductor track structures on the flow cannula 230. The webs 300 of the laser-structured spiral structure (see FIG. 3), which to a certain extent form the framework of the flexible flow cannula 230, leave windows 301 open. The windows 301 are preferably closed in a flexible manner, for example using silicone or polyurethane. The webs 300 together with the closed windows 301 form the hose guide of the flow cannula 230. According to the invention, electrical conductor track structures 302, 303 are applied to the webs 300 using lithography and coating technologies.

For the actual production of the electrical conductor tracks, a lithography mask comprising the corresponding coating structures (electrical conductor track structures) is applied for each layer. The lithography mask can be a chrome-coated quartz substrate, for example. Non-conductors such as photoresist or polyimide can be applied over a large area by dipping, for example. Non-conductors such as parylene C can be deposited in a vacuum, for example. Initial metallic layers are in particular applied by sputtering, thicker layers by electrodeposition.

There are two main approaches that can be used in the production process: According to Method 1, the tube material (for example NiTiNoI) is first provided with the electrical surface coating for the formation of the conductor tracks. In the next step, the flexible structure is produced, for example, by laser cutting (laser structuring), whereby the coating structure and the laser cutting contour are geometrically aligned to one another. In the last step, the windows of the flexible structure are closed, for example by dipping or overmolding. According to Method 2, the pipe material is structured first. The surface functionalization for the formation of the conductor tracks is then produced using the lithographic processes. Lastly, the windows of the flexible structure are closed as in Method 1. Method 1 has the advantage that the lithography process is simplified. Method 2 has the advantage that shape embossments in the NiTiNoI material are possible directly after the structuring of the pipe material; for example to "save" bends or cross-sectional changes to the cross-section of the starting material (e.g. widenings of the cross-section). Because of the process temperatures needed for the shape embossment, it is generally advantageous to perform this step before the lithographic surface coating.

Figure 5:
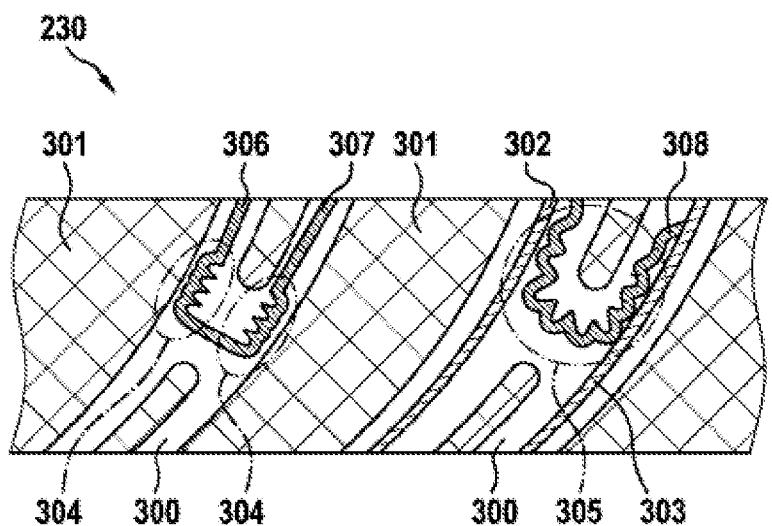
FIG. 5 a detail view of the hose guide of a flow cannula having a surface coating structure according to the invention with the configuration of sensor regions by the conductor tracks.

FIG. 5 shows particularly preferred configurations of the conductor tracks, in which the conductor track structure is designed as a sensor (left) or as an electrical connection and additionally as a sensor (right). As in FIG. 4, the flow cannula 230 is equipped with conductor tracks 302, 303, which are formed by surface structuring of the webs 300 of the flow cannula 230 (right part of the illustration). Meandering conductor tracks are provided as well, which form the sensor regions 304 (left) or the additional sensor region 305 (right). Straight sections of the conductor tracks can be provided between individual sensor regions 304, or the sensor region 305 is formed by a continuously meandering conductor track. The input and output lines 306, 307 of the sensor regions 304 can be made of a different material than the sensor regions themselves. A plurality of sensor regions can be implemented via separate input lines or even with a common return channel line 308, for example.

For a temperature sensor, for example, it can be provided that the conductor tracks of the sensor regions 304 or 305 are made of platinum, because platinum has a very linear resistance-temperature relationship. The input and output tracks 306, 307, 308 expediently have the lowest possible resistance in order to have little influence on the sensor signal. The conductor track structures can also be used as strain or breakage sensors, for example. They can also be used as capacitive sensors, electrode surfaces or contact pads for further sensors, for example.

Figure 6:
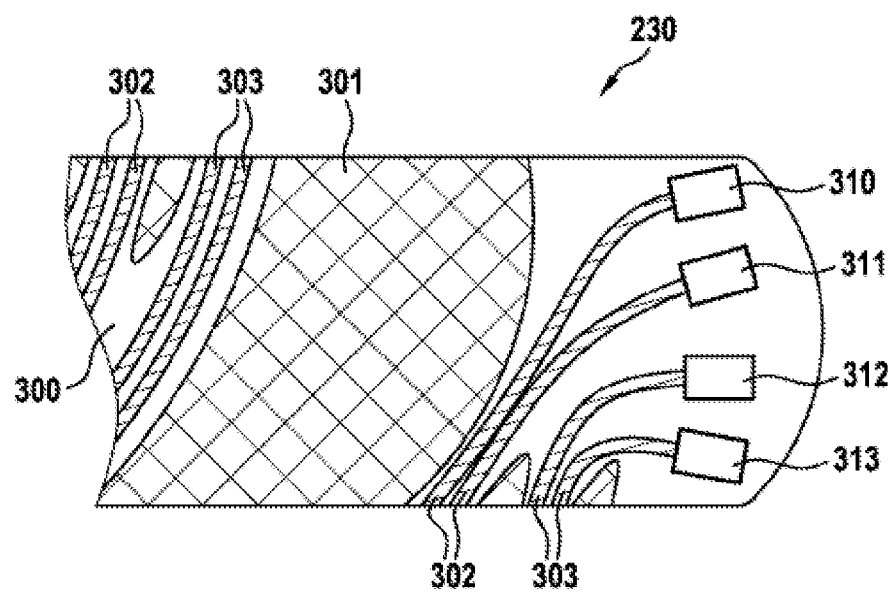
FIG. 6 a detail view of the hose guide of a flow cannula having a surface coating structure according to the invention showing electrical contact pads.

FIG. 6 shows a preferred electrical contacting of the conductor tracks 302, 303 via electrical contact pads 310, 311, 312, 313. This electrical contacting can take place, for example, at the end of the flow cannula 230, i.e. in the direction toward the second region 140. However, it is also possible for the conductor tracks to also be guided over other components of the blood pump, for example over the region 140, 150 to the electrical connection region 160. The electrical connection can be established by conductive gluing, soldering, bonding or frictional connection, for example. The connection can be made directly from NiTiNoI component to NiTiNoI component, for example, or from NiTiNoI component directly to a cable or a thin-film substrate, depending on the configuration of the blood pump.

Figure 7:
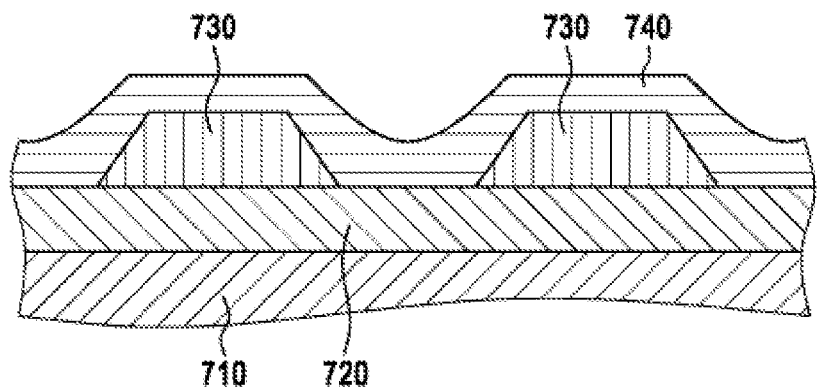
FIG. 7 a detail view of a cross-section through a flow cannula having a surface coating structure according to the invention.
Figure 8:
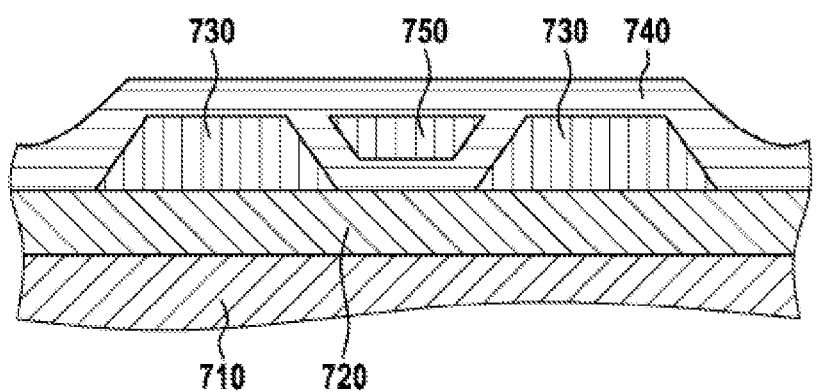
FIG. 8 a further detail view of a cross-section through a flow cannula having a surface coating structure according to the invention with a two-layer structure.

FIG. 7 shows a cross-section through the resulting layer structure that realizes the electrical conductor tracks. 710 represents the underlying NiTiNoI structure or another coatable material as the support structure of the flow cannula. 720 represents an insulating base layer, for example made of silicon oxide or polyimide. 730 shows the metallic conductor track structures, for example made of gold. 740 represents an insulating cover layer, for example made of silicon oxide, polyimide or parylene. A multilayer structure, for example a two-layer structure as illustrated in FIG. 8, can be created by repeating the surface coating several times (surface lithography). 710, 720, 730 and 740 represent the coatable structure, the insulating base layer, the first layer of the conductor track structures or the insulating cover layer, as in FIG. 7. A further conductor track 750 disposed at a slightly higher level is additionally provided in the spaces between the conductor track structures 730. During production, the space (empty space) between the conductor track structures 730 on the lower layer is used for the metallization of the upper layer by disposing the metallic conductor layer in this space. This offset arrangement of the conductor tracks on different levels prevents the formation of larger protrusions or roughnesses of the surface structure in the regions in which metallic conductor tracks would be on top of one another. This can occur in particular in higher multilayer structures having six or more layers. In this respect, this embodiment with an offset arrangement has the advantage over a purely coaxial embodiment that the resulting layer thickness of the conductor structure as a whole is reduced. This embodiment is also particularly advantageous compared to a coplanar design, because the overall conductor width is reduced. If an offset arrangement of the conductor tracks is not desired or possible, it is alternatively also possible to compensate any unevenness that may occur due to superimposed conductor tracks, for example with a silicone layer or the like.

Figure 9:
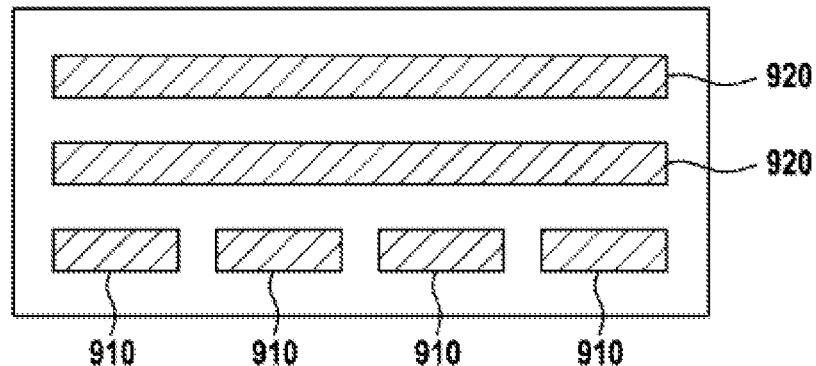
FIG. 9 a further detail view of a cross-section through a surface coating structure with a multilayer structure.
Figure 10:
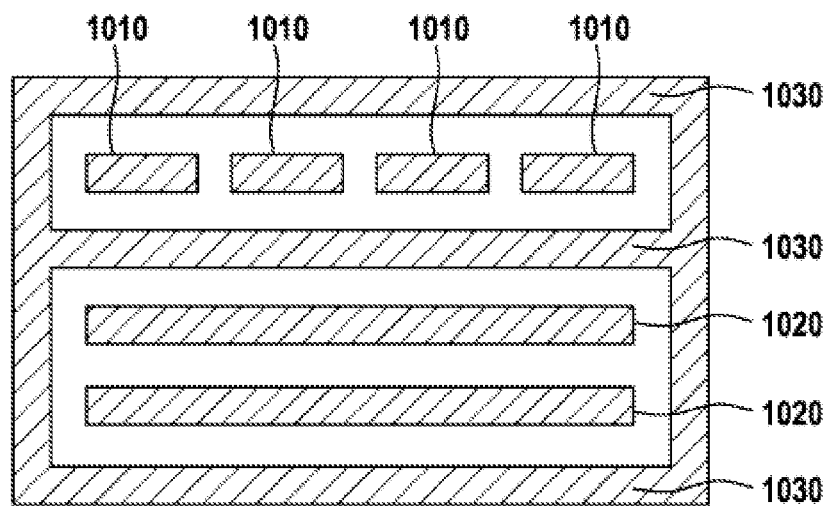
FIG. 10 a further detail view of a cross-section through a surface coating structure with a multilayer structure and shielding.

FIG. 9 shows a further structure of a multilayered conductor track structure. Four narrow conductor tracks 910 and two wide conductor tracks 920 are disposed one above the other on the coatable material (not shown in detail). The narrow conductor tracks 910 serve as a communication bus for a pressure sensor and a temperature sensor in the tip of the blood pump, for example. The wide conductor tracks 920 have a lower resistance (electrical power) and are used, for example, to connect an ultrasonic element in the tip of the blood pump. To produce such a structure, a total of seven layers are required for the surface coating. FIG. 10 shows a similar example of a 5 multilayered structure having four narrow conductor tracks 1010 and two wide conductor tracks 1020. Metallizations, which shield the conductor tracks 1010 and 1020 against one another and to the outside, are additionally provided as a shielding 1030, so that a defined line impedance and less high-frequency radiation are achieved along with a shielded routing of the signals. A total of 11 layers are required to produce such a structure. In the contact pad region, the up to 11 layers can expediently be widened accordingly and, for example, passed into the top metal layer through a vertical through-connection.

The invention claimed is:

1. A method of manufacturing electrical conductor tracks in a region of an intravascular blood pump, the method comprising:
providing the intravascular blood pump comprising:
a flow cannula comprising a spiral structure;
a sensor; and
an electrical connection region;
applying a conductor track structure to a coatable material of the flow cannula;
electrically connecting a first portion of the conductor track structure to the sensor;
electrically connecting a second portion of the conductor track structure to the electrical connection region; and
closing the spiral structure using a flexible material, wherein the flexible material comprises silicone or polyurethane.

2. The method of claim 1, wherein applying the conductor track structure comprises applying the conductor track structure about the spiral structure of the flow cannula.

3. The method according to claim 1, wherein providing the intravascular blood pump comprises providing the intravascular blood pump having the sensor disposed in a tip region of the intravascular blood pump.

4. The method according to claim 3, wherein the sensor comprises an ultrasonic element.

5. The method according to claim 3, wherein the sensor comprises a pressure sensor.

6. The method according to claim 3, wherein the sensor comprises a temperature sensor.

7. The method according to claim 1, wherein providing the intravascular blood pump comprises providing the intravascular blood pump having the sensor integrated into a surface coating structure of the intravascular blood pump.

8. The method according to claim 7, wherein the sensor comprises at least one of a strain sensor, a breakage sensor, and a temperature sensor.

9. The method according to claim 7, wherein applying the conductor track structure comprises applying one or more meandering conductor tracks forming one or more sensor regions of the sensor.

10. The method according to claim 9, wherein applying the one or more meandering conductor tracks forming the one or more sensor regions comprises applying a different material than one or more conductor tracks outside the sensor regions.

11. The method according to claim 9, wherein applying the one or more meandering conductor tracks forming the one or more sensor regions comprises applying platinum.

12. The method according to claim 1, wherein applying the conductor track structure to the coatable material comprises applying the conductor track structure to a material of the flow cannula comprising at least one of: nickel-titanium alloys, titanium, stainless steel, glass, and ceramic.

13. The method according to claim 1, wherein applying the conductor track structure comprises applying a multilayer structure.

14. The method according to claim 1, wherein electrically connecting at least the first portion or the second portion of the conductor track structure comprises forming a frictional connection.

15. The method according to claim 1, wherein applying the conductor track structure comprises:
    applying an insulating base layer to the coatable material;
    applying a photoresist material;
    applying the conductor track structure, wherein the conductor track structure is applied by sputtering;
    removing the photoresist material; and
    applying an electrically insulating surface, wherein the electrical insulating surface is biocompatible.

16. The method according to claim 15, wherein the intravascular blood pump further comprises:
    a tip;
    a first region comprising at least one blood through-opening;
    a flow cannula;
    a second region comprising at least one blood through-opening;
    a motor-operated pump device; and
    a conducting cable.

17. The method according to claim 16, wherein providing the intravascular blood pump comprises providing the intravascular blood pump having the sensor disposed in a tip region of the intravascular blood pump.

18. The method according to claim 1, wherein applying the conductor track structure comprises:
    applying an insulating base layer to the coatable material;
    applying an initial metallic conductor layer, wherein the initial metallic conductor layer is applied by sputtering;
    applying a photoresist material;
    thickening exposed portions of the initial metallic conductor layer using a wet chemical electroplating process;
    removing the photoresist material;
    removing portions of the initial metallic conductor layer outside conductor tracks;
    applying an electrically insulating surface, wherein the electrically insulating surface is biocompatible.

19. The method according to claim 18, wherein the intravascular blood pump further comprises:
    a tip;
    a first region comprising at least one blood through-opening;
    a flow cannula;
    a second region comprising at least one blood through-opening;
    a motor-operated pump device; and
    a conducting cable.

20. The method according to claim 19, wherein providing the intravascular blood pump comprises providing the intravascular blood pump having the sensor disposed in a tip region of the intravascular blood pump.

* * * * *